United States Patent

Fischer et al.

[11] 4,202,832
[45] May 13, 1980

[54] THIOCARBAMOYLTHIO FATTY ACIDS

[75] Inventors: Ulf Fischer, Frenkendorf; Ado Kaiser, Lausen, both of Switzerland

[73] Assignee: Hoffmann-La Roche Inc., Nutley, N.J.

[21] Appl. No.: 953,720

[22] Filed: Oct. 20, 1978

Related U.S. Application Data

[63] Continuation of Ser. No. 792,630, May 2, 1977, abandoned.

[51] Int. Cl.² .............. C07C 155/08; C07D 207/12; C07D 211/30; C07D 295/18
[52] U.S. Cl. ..................... 260/455 A; 260/326.83; 260/326.55; 546/233; 544/160
[58] Field of Search ......... 260/455 A, 326.83, 326.55; 546/233; 544/160

[56] References Cited

U.S. PATENT DOCUMENTS 1,726,646   9/1929   Codwell .................. 260/455 A

OTHER PUBLICATIONS

Archiv der Pharmazie, 296 (1963), No. 5, pp. 310–324.
Arzneimittelforschung 18, 10, 1968, pp. 1319–1324.

Primary Examiner—Henry R. Jiles
Assistant Examiner—Robert C. Whittenbaugh
Attorney, Agent, or Firm—Jon S. Saxe; George M. Gould; Peter R. Shearer

[57] ABSTRACT

Thiocarbamoylthio fatty acid derivatives of the formula

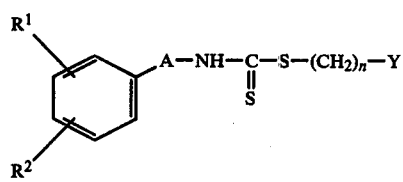

wherein $R^1$, $R^2$, A, Y and n are as hereinafter set forth, are described. The compounds of formula I are useful as lipid-lowering agents.

5 Claims, No Drawings

THIOCARBAMOYLTHIO FATTY ACIDS

This is a continuation, of application Ser. No. 792,630 filed May 2, 1977 now abandoned.

BRIEF SUMMARY OF THE INVENTION

The invention relates to thiocarbamoylthio fatty acid derivatives of the formula

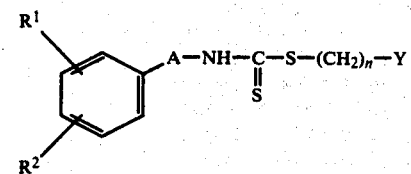
    I wherein $R^1$ and $R^2$, independently, are hydrogen, halogen, methyl, methoxy or p-chlorophenoxy; Y is cyano or a group of the formula

wherein $R^3$ is hydroxy, lower alkoxy, hydroxy-(lower alkoxy) or a group of the formula $—N(R^4)(R^5)$, wherein $R^4$ is hydrogen and $R^5$ is cycloalkyl containing from 3 to 6 carbon atoms, or $R^4$ and $R^5$, independently, are hydrogen or lower alkyl, or $R^4$ and $R^5$, when taken together with the nitrogen atom to which they are attached, are a 5- or 6-membered heterocyclic ring; A is methylene, ethylene, propylene or $—OCH_2CH_2—$; and n is an integer of from 2 to 10 inclusive, or, when Y is carboxy, salts thereof with pharmaceutically acceptable bases.

The compounds of formula I lower the blood fat level.

In another aspect, the invention relates to a process for the preparation of the compounds of formula I. In yet another aspect, the invention relates to pharmaceutical preparations containing the compounds of formula I.

DETAILED DESCRIPTION OF THE INVENTION

The invention relates to compounds of the formula

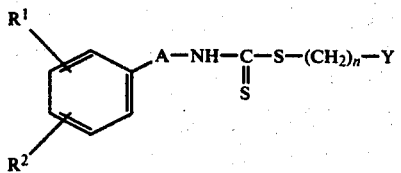
    I wherein $R^1$ and $R^2$, independently, are hydrogen, halogen, methyl, methoxy or p-chlorophenoxy; Y is cyano or a group of the formula

wherein $R^3$ is hydroxy, lower alkoxy, hydroxy-(lower alkoxy) or a group of the formula $—N(R^4)(R^5)$, wherein $R^4$ is hydrogen and $R^5$ is cycloalkyl containing from 3 to 6 carbon atoms, or $R^4$ and $R^5$, independently, are hydrogen or lower alkyl, or $R^4$ and $R^5$, when taken together with the nitrogen atom to which they are attached, are a 5- or 6-membered heterocyclic ring; A is methylene, ethylene, propylene or $—OCH_2CH_2—$; and n is an integer from 2 to 10 inclusive, or, when Y is carboxy, salts thereof with pharmaceutically acceptable bases.

As used herein, the term "lower alkyl" denotes a straight or branched chain saturated hydrocarbon containing 1 to 7 carbon atoms, for example, methyl, ethyl, propyl, isopropyl, butyl, t-butyl, neopentyl, pentyl, heptyl or the like. The term "lower alkoxy" denotes an alkyloxy in which the alkyl group is as described above, for example, methoxy, ethoxy, propoxy, pentoxy, or the like. The term "halogen" denotes all the halogens, i.e., bromine, chlorine, fluorine or iodine. Exemplary of the group $—N(R^4)(R^5)$ are amino, monomethylamino, dimethylamino, monoethylamino, diethylamino, monocyclopropylamino, monocyclobutylamino, monocyclopentylamino, monocyclohexylamino, pyrrolidino, piperidino or morpholino.

A preferred group of compounds of formula I comprises those wherein $R^1$ is hydrogen, namely, those compounds which are unsubstituted or monosubstituted in the phenyl ring. Other preferred compounds of formula I are those wherein $R^2$ is halogen, preferably chlorine, and Y is

preferably lower alkoxycarbonyl or carboxy, as well as those wherein A is methylene and n is 2, 3 or 4, preferably 3. A more preferred compound of formula I is 4-{[(p-chlorobenzyl)thiocarbamoyl]thio}-butyric acid ethyl ester.

The compounds of formula I wherein Y is —COOH form salts with pharmaceutically acceptable bases. Exemplary of the salts of the acids of formula I are ammonium salts, alkali metal salts, such as the sodium or potassium salts, alkaline earth metal salts, such as calcium salts, and salts with amines, such as monoalkylamines, dialkylamines or trialkylamines.

According to the process of the present invention, the thiocarbamoylthio fatty acid derivatives, i.e., the compounds of formula I of the invention, and salts of such compounds, wherein Y is carboxy, with bases, can be prepared by reacting a compound of the formula

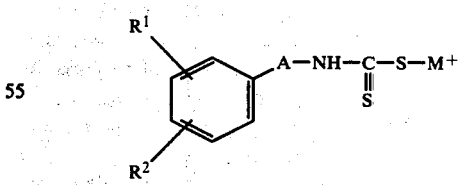
    II wherein $R^1$, $R^2$ and A are as previously described and $M^+$ is $Na^+$, $K^+$ or $NH_4^+$,
with a compound of the formula

    III wherein X is halogen and Y and n are as previously described, or with an alkali metal salt of a halocarboxylic acid of the formula

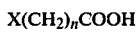
X(CH$_2$)$_n$COOH   IV wherein X and n are as previously described, or reacting an isothiocyanate of the formula

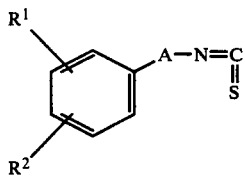
V wherein R$^1$, R$^2$ and A are as previously described, with a mercaptan of the formula

HS—(CH$_2$)$_n$—Y   VI wherein Y and n are as previously described, and, if desired, saponifying an ester so obtained or an amide so obtained to an acid, reesterifying an ester obtained, esterifying an acid so obtained or converting same into a salt with a base, hydrolyzing a nitrile so obtained to an amide or dehydrating an amide so obtained to a nitrile.

The reaction of a compound of formula II with a compound of formula III is conveniently carried out in an inert solvent, such as water, acetone, an alcohol, dimethylformamide, dioxane or dioxane/water. The reaction can be carried out at room temperature, although in certain cases it may be convenient to warm the reaction mixture.

The reaction of an isothiocyanate of formula V with a mercaptan of formula VI is conveniently carried out in an inert solvent, for example, toluene, or an ether, such as dioxane, at a temperature in the range of from about −20° C. to the reflux temperature of the reaction mixture, preferably at about 0° C.

The optional subsequent transformations at the group Y can be carried out in accordance with methods known per se. The saponification of an ester or amide of formula I to an acid of formula I can be carried out, for example, with dilute acids, such as half-concentrated hydrochloric acid, conveniently while warming. The esterification of an acid of formula I can be carried out by reacting a suspension or solution of said acid with an excess of alcohol and thionyl chloride at a temperature in the range of from about 0° C. to about room temperature. The preparation of a salt of an acid of formula I can be carried out by reacting the acid with the stoichiometric amount of a base, such as an alkali metal hydroxide, ammonium hydroxide, an alkaline earth metal hydroxide, ammonium hydroxide, an alkaline earth metal hydroxide or an amine. A nitrile of formula I can be hydrolyzed to a corresponding amide of formula I using an acid such as hydrochloric acid or sulfuric acid. An amide of formula I can be dehydrated to a corresponding nitrile of formula I using phosphorus oxychloride or thionyl chloride and dimethylformamide.

The compounds of formula II can be prepared by reacting a compound of the formula

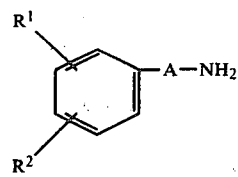
VII wherein R$^1$, R$^2$ and A are as previously described, with sodium hydroxide, potassium hydroxide or ammonium hydroxide and carbon disulfide. This reaction is preferably carried out in a water-miscible inert solvent such as acetonitrile at a low temperature, for example, in the range of from about 0° C. to room temperature.

The compounds of formulas III, IV, V, VI and VII are known compounds or can be prepared in an analogous manner to known compounds.

The thiocarbamoylthio fatty acid derivatives provided by the invention can be utilized as medicaments, particularly as lipid-lowering agents, due to their activity in lowering the blood fat level. When 4-{[(p-chlorobenzyl)thiocarbamoyl]thio}-butyric acid ethyl ester is repeatedly administered to male rats (5 times at a rate of 90 mg/kg p.o.) there was brought about, for example, a 30–40% reduction of triglyceride and a 20–30% reduction of cholesterol in serum taken from the rats. This result is achieved with half of the dosage which would be required using the known lipid-lowering agent clofibrate ("Merck Index," 1968, page 270). For administration to a warm-blooded animal requiring such treatment, there come into consideration dosages of 30 to 60 mg of a thiocarbamoylthio fatty acid derivative of formula I of the invention per kg of body weight.

The thiocarbamoylthio fatty acid derivatives of formula I of the invention and the salts thereof with pharmaceutically acceptable bases can be used as medicaments. For example, they can be used in the form of pharmaceutical preparations which contain them in association with one or more compatible pharmaceutical carrier materials. Such carrier materials can be an inert organic or inorganic carrier material suitable for enteral or parenteral administration, for example, water, gelatin, gum arabic, lactose, starch, magnesium stearate, talc, vegetable oils, polyalkyleneglycols, or the like. The pharmaceutical preparations can be made up in a solid form, for example, as tablets, dragees or capsules, or in a liquid form, for example, as solutions, suspensions or emulsions. The pharmaceutical preparations may be sterilized and/or may contain adjuvants, such as preserving, stabilizing, wetting or emulsifying agents, salts for varying osmotic pressure or buffers. The pharmaceutical preparations may also contain therapeutically valuable substances other than the thiocarbamoylthio fatty acid derivatives provided by this invention.

The Examples which follow further illustrate the invention. All temperatures are in degrees centigrade, unless otherwise mentioned.

EXAMPLE 1

Preparation of 4-{[(p-chlorobenzyl)thiocarbamoyl]thio}-butyric acid ethyl ester

To a solution of 160 g. of 4-bromobutyric acid ethyl ester in 1125 ml. of absolute dimethylformamide were added gradually under an atmosphere of argon at 0° C.

while stirring well and cooling, 172.3 g. of ammonium (N-4-chlorobenzyl)dithiocarbamate, the temperature was maintained constant. The slightly yellow solution was stirred overnight at room temperature, diluted with 1500 ml. of water and extracted four times with 500 ml. of ethyl acetate each time. The combined organic phases were washed three times with 200 ml of saturated sodium chloride solution each time and dried over 80 g. of magnesium sulfate with the addition of carbon, filtered and evaporated under reduced pressure. The resulting crystalline residue was recrystallized from 700 ml. of diisopropyl ether, and 218 g. of 4-{[(p-chlorobenzyl)thiocarbamoyl]thio}-butyric acid ethyl ester having a melting point of 61°-62° C. was obtained.

The dithiocarbamate utilized as the starting material can be prepared as follows:

260 ml. of concentrated ammonia solution were treated under an atmosphere of argon, and while cooling by means of ice/methanol bath at $\leq -10°$ C. within about 20 minutes, with 164.5 g. of carbon disulfide and the mixture was subsequently stirred for an additional 15 minutes at the same temperature. 245 G. of 4-chlorobenzylamine dissolved in 122 ml. of acetonitrile were then slowly added, the temperature still maintained at $\leq -10°$ C. Subsequently, the mixture was stirred overnight at room temperature and then cooled in an ice-bath to 0° C. The precipitated crystals were removed by filtration under suction, washed successively with acetonitrile and diethyl ether and dried to a constant weight under reduced pressure at 70°-80° C., and 390 g. of ammonium (N-4-chlorobenzyl)dithiocarbamate having a melting point of 140°-142° C. was obtained.

In an analogous manner to that described above, the following thiocarbamoylthio fatty acid derivatives were prepared:

4-[(benzylthiocarbamoyl)thio]-butyric acid ethyl ester having a melting point of 56°-57° C.;

3-{[(p-chlorobenzyl)thiocarbamoyl]thio}-propionic acid ethyl ester having a melting point of 67°-68° C.;

11-{[(p-chlorobenzyl)thiocarbamoyl]thio}-undecanoic acid ethyl ester having a melting point of 51.5°-52.5° C.;

5-{[(p-chlorobenzyl)thiocarbamoyl]thio}-valeric acid ethyl ester having a boiling point of 135°-137° C./0.08 Torr;

4-{[(2,5-dichlorobenzyl)thiocarbamoyl]thio}-butyric acid ethyl ester having a melting point of 62°-63° C.;

4-{[(p-methoxybenzyl)thiocarbamoyl]thio}-butyric acid ethyl ester having a melting point of 47°-48° C.;

4-{[(p-methylbenzyl)thiocarbamoyl]thio}-butyric acid ethyl ester having a melting point of 61°-62° C.;

4-{[[2-(p-chlorophenoxyphenoxy)ethyl]thiocarbamoyl]thio}-butyric acid ethyl ester having a melting point of 72°-74° C.; and 4-{[[2-(p-chlorophenoxy)-ethyl]thiocarbamoyl]thio}-butyric acid ethyl ester having a melting point of 63°-64° C.

EXAMPLE 2

Preparation of 4-{[[3-(p-chlorophenyl)propyl]thiocarbamoyl]thio}-butyric acid ethyl ester 20.3 G. of ammonium 3-[(p-chlorophenyl)propyl]dithiocarbamate were added slowly while cooling with ice to a solution of 12.4 ml. of 4-bromobutyric acid ethyl ester in 120 ml. of ethanol and the mixture was stirred overnight at room temperature. After evaporation in vacuo, the residue was partitioned between water and ethyl acetate, the aqueous phase extracted three times with ethyl acetate, the combined organic phases washed with saturated sodium chloride solution, dried over magnesium sulfate and again concentrated in vacuo. The remaining oily residue was chromatographed on silica gel using toluene/ethyl acetate for the elution, and 19.0 g. of 4-{[[3-(p-chlorophenyl)-propyl]thiocarbamoyl]thio}-butyric acid ethyl ester, as a colorless viscous oil, were obtained.

4-{[(p-chlorophenethyl)thiocarbamoyl]thio}-butyric acid ethyl ester was prepared in the form of an oil in an analogous manner to that described in the preceding paragraph.

EXAMPLE 3

Preparation of 4-{[[(p-chlorophenyl)propyl]-thiocarbamoyl]thio}-butyric acid

10 G. of 4-{[[3-(p-chlorophenyl)propyl]thiocarbamoyl]-thio}-butyric acid ethyl ester dissolved in 100 ml. of acetic acid were stirred under slight reflux for 8 hours with 50 ml. of half-concentrated hydrochloric acid. The mixture was evaporated in vacuo, the residue recrystallized from carbon tetrachloride, and 4.4 g. of 4-{[[(p-chlorophenyl)propyl]-thiocarbamoyl]thio}-butyric acid having a melting point of 98°-100° C. were obtained.

The following thiocarbamoylthio fatty acid derivatives were prepared in a corresponding manner:

4-{[(p-chlorophenethyl)thiocarbamoyl]thio}-butyric acid having a melting point of 112°-113° C.;

3-{[(p-chlorobenzyl)thiocarbamoyl]thio}-propionic acid having a melting point of 126°-127° C.; and 4-{[(p-chlorobenzyl)thiocarbamoyl]thio}-butyric acid having a melting point of 104°-105° C.

EXAMPLE 4

Preparation of 3-cyanopropyl(p-chlorobenzyl)dithiocarbamate

To 37.5 g. of 4-bromobutyronitrile in 350 ml. of absolute dimethylformamide were added, while cooling with ice, 53.7 g. of ammonium (N-4-chlorobenzyl)dithiocarbamate and the mixture was stirred overnight at room temperature. After evaporation in vacuo, the product was taken up in ethyl acetate, washed with water, dried, concentrated and the residue crystallized from diethyl ether/diisopropyl ether, whereby 48.2 g. of 3-cyanopropyl(p-chlorobenzyl)dithiocarbamate having a melting point of 61°-63° C. were obtained.

EXAMPLE 5

Preparation of 3-carbamoylpropyl(p-chlorobenzyl)dithiocarbamate 29.2 G. of 3-cyanopropyl(p-chlorobenzyl)dithiocarbamate were suspended in 150 ml. of concentrated hydrochloric acid and stirred at room temperature for 2 hours. The mixture was diluted with water and extracted with ethyl acetate. After washing, drying and concentration of the ethyl acetate phases, 18.1 g. of 3-carbamoylpropyl)p-chlorobenzyl)dithiocarbamate were crystallized from ethyl acetate/diisopropyl ether; melting point 123°-125° C.

EXAMPLE 6

Preparation of 3-(methylcarbamoyl)-propyl(p-chlorobenzyl)dithiocarbamate 15.8 G. of γ-chloro-N-methylbutyric acid amide dissolved in 200 ml. of absolute ethanol were treated with 24.8 g. of ammonium (N-4-chlorobenzyl)dithiocarbamate. After a clear solution had formed, it was stirred at 60° C. for 1.5 hours. Thereafter, it was concentrated in vacuo, and the residue taken up in water and extracted with ethyl acetate. The organic phases were washed with saturated sodium chloride solution, dried over magnesium sulfate and concentrated. The residue was crystallized from ethyl acetate/diisopropyl ether, and 12.7 g. of 3-(methylcarbamoyl)-propyl(p-chlorobenzyl)-dithiocarbamate, having a melting point of 139°–141° C. were obtained.

The following thiocarbamoylthio fatty acid derivatives were prepared in an analogous manner:

3-(ethylcarbamoyl)propyl(p-chlroobenzyl)dithiocarbamate having a melting point of 117°–119° C.;

3-(diethylcarbamoyl)propyl(p-chlorobenzyl)dithiocarbamate having a melting point of 71°–73° C.;

3-(cyclohexylcarbamoyl)propyl(p-chlorobenzyl)dithiocarbamate having a melting point of 109°–111° C.;

3-(piperidinocarbonyl)propyl(p-chlorobenzyl)dithiocarbamate having a melting point of 82°–86° C.;

3-(morpholinocarbonyl)propyl(p-chlorobenzyl)dithiocarbamate having a melting point of 102°–104° C.;

3-(phenethylcarbamoyl)propyl(p-chlorobenzyl)dithiocarbamate having a melting point of 118°–120° C.; and 3-[(p-chlorophenethyl)carbamoyl]propyl(p-chlorobenzyl)-dithiocarbamate having a melting point of 123°–125° C.

EXAMPLE 7

Preparation of 4-{[(p-chlorobenzyl)thiocarbamoyl]thio}-butyric acid methyl ester 1.5 G. of 4-{[(p-chlorobenzyl)thiocarbamoyl]thio}-butyric acid were dissolved in 30 ml. of diethyl ether and treated with an excess of an ethereal diazomethane solution. The resulting solution was evaporated. The residue was recrystallized from cyclohexane, and 1.2 g. of 4-{[(p-chlorobenzyl)thiocarbamoyl]thio}-butyric acid methyl ester having a melting point of 60°–62° C. were obtained.

EXAMPLE 8

Preparation of 4-{[(p-chlorobenzyl)thiocarbamoyl]thio}-butyric acid 2-hydroxyethyl ester 9.15 G. of 4-{[(p-chlorobenzyl)thiocarbamoyl]thio}-butyric acid dissolved in 120 ml. of ethyleneglycol were treated dropwise at −5° C. with 8.7 ml. of thionyl chloride and the mixture was subsequently stirred at room temperature for 3 hours. Then, the solution was made alkaline with 2-N sodium hydroxide solution and extracted with chloroform. The chloroform phases were washed with saturated sodium chloride solution, dried over magnesium sulfate and concentrated. Recrystallization of the residue from diisopropyl ether gave 8.1 g. of 4-{[(p-chlorobenzyl)thiocarbamoyl]thio}-butyric acid 2-hydroxyethyl ester having a melting point of 77°–78° C.

The following thiocarbamoylthio fatty acid derivatives were prepared in an analogous manner:

4-{[(p-chlorobenzyl)thiocarbamoyl]thio}-butyric acid isopropyl ester having a melting point of 76°–77° C.;

4-{[(p-chlorobenzyl)thiocarbamoyl]thio}-butyric acid butyl ester having a melting point of 66°–67° C.; and 4-{[(p-chlorophenethyl)thiocarbamoyl]thio}-butyric acid 2-hydroxyethyl ester having a melting point of 69°–70° C.

EXAMPLE 9

Preparation of 3-{[(p-chlorobenzyl)thiocarbamoyl]thio}-propionic acid

To a solution of 1.06 g. of 3-mercaptopropionic acid in 5 ml. of toluene and 2.0 g. of triethylamine, there was added with cooling 1.83 g. of p-chlorobenzylisothiocyanate. Two phases formed. The mixture was acidified with 1-N hydrochloric acid and extracted with chloroform. The chloroform phases were washed with water, dried over magnesium sulfate and concentrated. The residue was recrystallized from acetonitrile, and 2.1 g. of 3-{[(p-chlorobenzyl)thiocarbamoyl]thio}-propionic acid having a melting point of 126°–127° C. were obtained.

3-{[(p-Chlorophenethyl)thiocarbamoyl]thio}-propionic acid having a melting point of 104.5°–105° C. was prepared in an analogous manner.

The following Example illustrates a pharmaceutical preparation containing the thiocarbamoylthio fatty acid derivatives provided by the invention:

EXAMPLE A

Tablets containing the following ingredients were produced in a manner known per se:

| Ingredient | Per Tablet |
| --- | --- |
| 4-{[(p-chlorobenzyl)thiocarbamoyl]-thio}-butyric acid ethyl ester | 50.00 mg. |
| Polyethyleneglycol | 200.00 mg. |
| Lactose | 70.00 mg. |
| Microcrystalline cellulose | 70.00 mg. |
| Polyvinylpyrrolidone | 100.00 mg. |
| Magnesium stearate | 10.00 mg. |
| Total Weight | 500.00 mg. |

We claim:

1. A compound of the formula

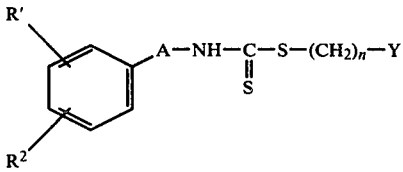

wherein $R^1$ is hydrogen, and $R^2$ is halogen; Y is a group of the formula

wherein $R^3$ is hydroxy, lower alkoxy, hydroxy-(lower alkoxy) or a group of the formula —$N(R^4)(R^5)$, wherein $R^4$ is hydrogen and $R^5$ is cycloalkyl containing 3 to 6 carbon atoms, or $R^4$ and $R^5$, independently, are hydrogen or lower alkyl, or $R^4$ and $R^5$, when taken together with the nitrogen atom to which they are attached, are a pyrrolidino, piperidino or morpholino ring; A is methylene, ethylene, propylene or —$OCH_2CH_2$—; and n is 3, or, when Y is carboxy, salts thereof with pharmaceutically acceptable bases.

2. A compound in accordance with claim 1, wherein $R^3$ is hydroxy, lower alkoxy, hydroxy-(lower alkoxy)-, or a group of the formula —$N(R^4)(R^5)$, wherein $R^4$ and $R^5$, independently, are hydrogen or lower alkyl, or $R^4$ and $R^5$, when taken together with the nitrogen atom to which they are attached, are a pyrrolidino, piperidino or morpholino ring.

3. A compound in accordance with claim 2, wherein $R^2$ is chlorine and $R^3$ is hydroxy or lower alkoxy.

4. A compound in accordance with claim 3, wherein A is methylene.

5. A compound in accordance with claim 1, 4-{[(p-chlorobenzyl)thiocarbamoyl]-thio}-butyric acid ethyl ester.

* * * * *